United States Patent
Tsuji et al.

(10) Patent No.: US 11,857,724 B2
(45) Date of Patent: Jan. 2, 2024

(54) CPAP APPARATUS

(71) Applicant: Murata Manufacturing Co., Ltd., Kyoto (JP)

(72) Inventors: Shigeru Tsuji, Kyoto (JP); Takanori Hayashi, Kyoto (JP); Hiroaki Wada, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 593 days.

(21) Appl. No.: 16/904,718

(22) Filed: Jun. 18, 2020

(65) Prior Publication Data

US 2020/0316329 A1 Oct. 8, 2020

Related U.S. Application Data

(63) Continuation of application No. PCT/JP2018/046026, filed on Dec. 14, 2018.

(30) Foreign Application Priority Data

Dec. 20, 2017 (JP) .................................. 2017-243885

(51) Int. Cl.
*A61M 16/00* (2006.01)

(52) U.S. Cl.
CPC ...... *A61M 16/024* (2017.08); *A61M 16/0003* (2014.02); *A61M 16/0066* (2013.01);
(Continued)

(58) Field of Classification Search
None
See application file for complete search history.

(56) References Cited

U.S. PATENT DOCUMENTS 6,968,842 B1 * 11/2005 Truschel ............. A61M 16/024
128/204.23
10,668,236 B2    6/2020 Nathan et al.
(Continued)

FOREIGN PATENT DOCUMENTS

JP  H10-507116 A   7/1998
JP  2008-514287 A   5/2008
(Continued)

OTHER PUBLICATIONS

International Search Report for International Application No. PCT/JP2018/046026, dated Jan. 29, 2019.
(Continued)

*Primary Examiner* — Philip R Wiest
*Assistant Examiner* — Nathan M Le
(74) *Attorney, Agent, or Firm* — Pearne & Gordon LLP (57) ABSTRACT

A CPAP apparatus according to the present disclosure includes a housing, a hose whose one end communicates with a connection portion, a fan configured to expel air flowing in from an intake port, from another end of the hose, a motor and a motor driving unit configured to rotationally drive the fan, a control unit configured to control the motor driving unit, and a flow rate sensor. The control unit includes a command generation unit configured to generate a command value of a rotation number of the fan such that a pressure to be expelled from the other end of the hose becomes a target pressure, and a command correction unit configured to correct the command value based on a flow rate value obtained by the flow rate sensor.

9 Claims, 7 Drawing Sheets

(52) U.S. Cl.
CPC .............. *A61M 2016/003* (2013.01); *A61M 2016/0027* (2013.01); *A61M 2205/103* (2013.01); *A61M 2205/3334* (2013.01); *A61M 2205/502* (2013.01)

(56) References Cited

U.S. PATENT DOCUMENTS

| | | | |
|---|---|---|---|
| 2001/0035186 A1* | 11/2001 | Hill ...................... | A61M 16/00 128/204.23 |
| 2002/0005197 A1 | 1/2002 | Devries et al. | |
| 2006/0065270 A1* | 3/2006 | Li ........................ | A61M 16/026 128/204.23 |
| 2008/0251079 A1* | 10/2008 | Richey ............... | A61M 16/0666 128/204.26 |
| 2012/0227738 A1* | 9/2012 | Virr ................... | A61M 16/1095 128/204.21 |
| 2015/0165146 A1* | 6/2015 | Bowman ............... | A61M 16/16 128/203.14 |
| 2015/0265787 A1* | 9/2015 | O'Connor ............. | A61M 16/06 128/204.23 |
| 2017/0093063 A1* | 3/2017 | Lee ...................... | H01R 12/716 |
| 2017/0211438 A1 | 7/2017 | Suzuki et al. | |
| 2018/0093063 A1* | 4/2018 | Rajan ................ | A61M 16/0066 |
| 2018/0221606 A1* | 8/2018 | Brandt ............. | A61M 16/0066 |

FOREIGN PATENT DOCUMENTS

| | | |
|---|---|---|
| JP | 2015-534496 A | 12/2015 |
| JP | 2016-034411 A | 3/2016 |

OTHER PUBLICATIONS

Written Opinion for International Application No. PCT/JP2018/046026, dated Jan. 29, 2019.

\* cited by examiner

CPAP APPARATUS

This is a continuation of International Application No. PCT/JP2018/046026 filed on Dec. 14, 2018 which claims priority from Japanese Patent Application No. 2017-243885 filed on Dec. 20, 2017. The contents of these applications are incorporated herein by reference in their entireties.

BACKGROUND

Technical Field

The present disclosure relates to a CPAP apparatus.

A sleep apnea syndrome in which respiration stops during sleep has been attributed to physically narrowing the upper airway which is a passage of air and stopping the respiration. As therapy effective for the sleep apnea syndrome, there is therapy using a Continuous Positive Airway Pressure (CPAP) apparatus. The CPAP apparatus is an apparatus that continues to deliver air to the airway to open the airway in order to prevent apnea during sleep.

The CPAP apparatus continues to deliver air to the airway of a patient wearing a mask to open the airway by delivering air to the mask that is worn over the nose or mouth through an air tube. For this reason, the CPAP apparatus controls air to be delivered to the mask in order to open the airway by continuing to deliver air to the airway of the patient. Specific control is disclosed in, for example, Patent Document 1.

Patent Document 1: Japanese Unexamined Patent Application Publication (Translation of PCT Application) No. 2015-534496

BRIEF SUMMARY

Technical Problem

In an apparatus described in Patent Document 1, a processing module is provided to control air to be delivered to a mask, and the processing module continuously estimates a decrease in pressure between an output portion and an expelling point of pressurized air. Furthermore, the apparatus described in Patent Document 1 performs control to compensate for the decreased pressure such that the pressurized air becomes a target pressure based on the estimated result.

However, even when a conventional CPAP apparatus performs control to pressurize air such that the air becomes the target pressure, in a case where a disturbance, such as a flow rate of inhalation or exhalation of a patient is large, the target pressure may not be sufficiently compensated.

The present disclosure provided a CPAP apparatus capable of controlling a pressure of air to be expelled so as to become a target pressure, regardless of disturbance.

A CPAP apparatus according to one embodiment of the present disclosure includes a housing having an intake inlet and an exhaust outlet, an air passage member having one end communicating with the exhaust outlet, a fan configured to expel air flowing in from the intake inlet, from another end of the air passage member, a driving unit configured to rotationally drive the fan, a control unit configured to control the driving unit, and a flow rate measuring unit configured to measure a flow rate of air between the fan and the other end of the air passage member, in which the control unit includes a command generation unit configured to generate a command value of a rotation number of the fan at which a pressure of air to be expelled from the exhaust outlet becomes a target pressure, and a command correction unit configured to correct the command value based on a flow rate value obtained by the flow rate measuring unit.

According to the present disclosure, since a command value is corrected based on a flow rate value obtained by the flow rate measuring unit, a pressure of air to be expelled can be controlled to become a target pressure, regardless of disturbance.

DETAILED DESCRIPTION

Hereinafter, a CPAP apparatus according to an embodiment of the present disclosure will be described in detail with reference to the accompanying drawings. Note that in the drawings, the same reference signs indicate the same or corresponding portions.

(Configuration of Apparatus)

Figure 1:
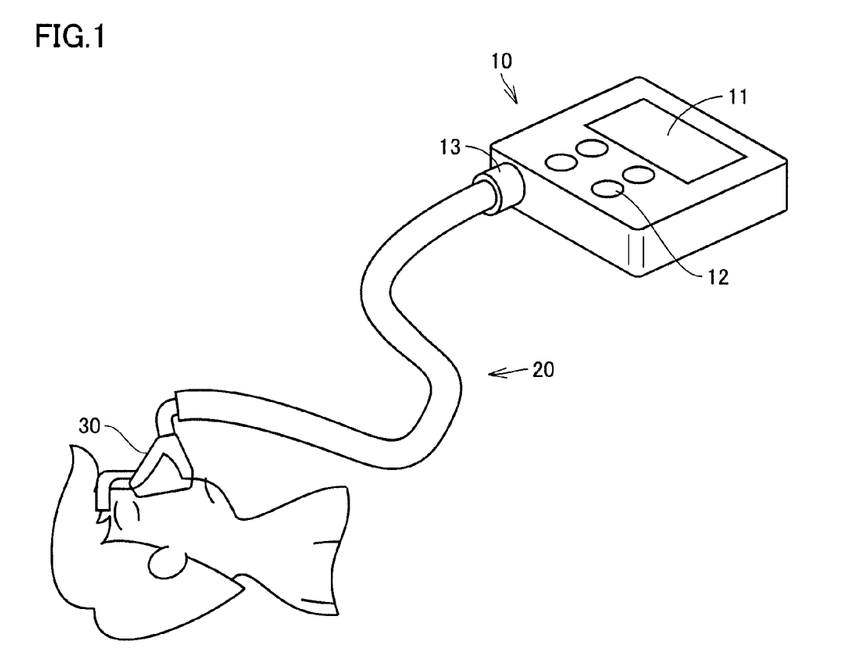
FIG. 1 is a schematic diagram for explaining a configuration of a CPAP apparatus according to an embodiment of the present disclosure.
Figure 2:
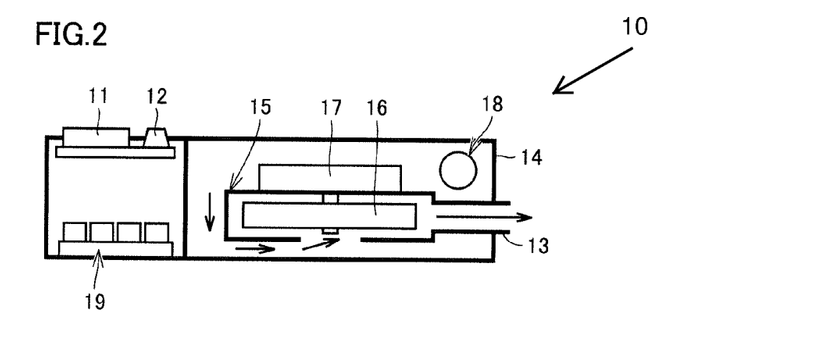
FIG. 2 is a cross-sectional view for explaining the configuration of the CPAP apparatus according to the embodiment of the present disclosure.

FIG. 1 is a schematic diagram for explaining a configuration of a CPAP apparatus 10 according to the embodiment of the present disclosure. FIG. 2 is a cross-sectional view for explaining the configuration of the CPAP apparatus 10 according to the embodiment of the present disclosure. FIG. 1 shows an overview when the CPAP apparatus 10 is used for a patient. When the CPAP apparatus 10 is used for a patient, a mask 30 to be worn by the patient and a hose 20 for delivering air from the CPAP apparatus 10 to the mask 30 are required.

The hose 20 is attachable to and detachable from the CPAP apparatus 10. As shown in FIG. 1, the mask 30 is applied and fixed so as to cover the nose of the patient. Note that as the mask 30, a mask having a shape or a structure suitable for the patient can be selected from among various types, and a shape and a structure shown in FIG. 1 are an example.

The CPAP apparatus 10 is provided with a display unit 11 for displaying a state and an operation method of the apparatus, and the like, a plurality of operation buttons 12, and a connection portion 13 for connecting the hose 20. The connection portion 13 configures an exhaust outlet, and the hose 20 configures an air passage member whose one end communicates with the exhaust outlet. The display unit 11 is configured with, for example, an LCD, but may be a seven-segment LED, an organic EL display, or the like. Further, the operation buttons 12 may not necessarily be a switch having a physical shape as shown in the figure, and may be a touch panel or the like provided on a display surface of the LCD.

The CPAP apparatus 10 further has a structure to deliver air to the mask 30. Note that in FIG. 2, for simplicity of explanation, the structure is simplified and a structure for delivering air is shown on a right side of the display unit 11 and the operation button 12. Therefore, arrangement of the display unit 11, the operation button 12, and the structure for delivering air in the CPAP apparatus 10 is not limited to the arrangement shown in FIG. 2.

An air supply unit 15 is provided inside a housing 14 of the CPAP apparatus 10 in order to deliver air from the connection portion 13 to the hose 20. A fan 16 is provided in the air supply unit 15, and the fan 16 is driven by a motor 17. The air supply unit 15 drives the fan 16, so that air in the housing 14 is taken from a lower portion of the air supply unit 15 as indicated by the arrow in FIG. 2, and is expelled from the connection portion 13 to the hose 20. Also, the housing 14 is provided with an intake port 18 serving as an intake inlet, and air is taken into the housing 14 from the outside via the intake port 18.

The CPAP apparatus 10 may be provided with a silencer (not shown) in the air supply unit 15. The silencer is mounted near an air flow outlet of the air supply unit 15, and plays a role of reducing outflow noise of air flowing out from the air supply unit 15 and passing through the air flow outlet. Further, the silencer can utilize a space from the intake port 18 to an inlet of the fan 16, so that a silencing effect can be exhibited.

Figure 3:
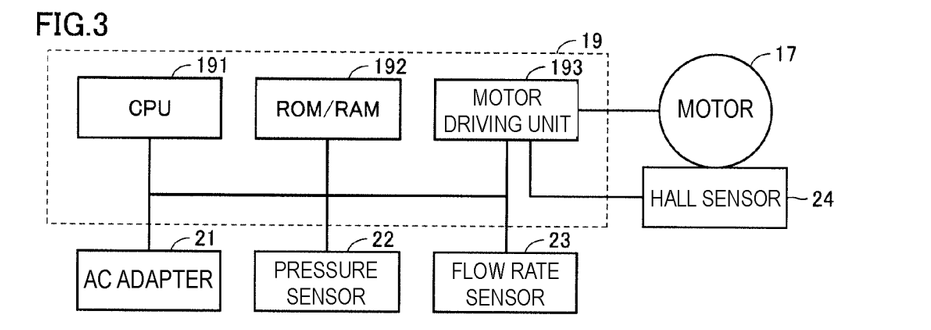
FIG. 3 is a block diagram for explaining a configuration of a control board of the CPAP apparatus according to the embodiment of the present disclosure.

Furthermore, the CPAP apparatus 10 includes a control board 19 on which circuits for performing display control of the display unit 11, reception of an operation of the operation buttons 12, control of the motor 17 for rotating the fan 16, and the like are mounted. FIG. 3 is a block diagram for explaining a configuration of the control board 19 of the CPAP apparatus 10 according to the embodiment of the present disclosure. The control board 19 includes a CPU 191 for executing a program, a ROM/RAM 192, and a motor driving unit 193 as main constituent elements. The ROM/RAM 192 includes a ROM for storing data in a nonvolatile manner, and a RAM for storing data generated by execution of the program by the CPU 191 or data input by using the operation buttons 12. The respective constituent elements of the control board 19 are connected to each other with a data bus.

Processing in the CPU 191 is implemented by each piece of hardware and software executed by the CPU 191. Such software is stored in advance in the ROM/RAM 192. The display control of the display unit 11, the reception of the operation of the operation buttons 12, the control of the motor 17 for rotating the fan 16, and the like are also implemented by the software.

An AC adapter 21 for supplying electric power is connected to the control board 19, and a pressure sensor 22 and a flow rate sensor 23 are also connected to the control board 19. The pressure sensor 22 is a sensor for measuring a pressure of air expelled by the air supply unit 15. In addition, the pressure sensor 22 measures a pressure in an air flow path (air passage) including the CPAP apparatus 10 and an air passage member (hose 20) that communicates with an exhaust outlet (connection portion 13), so that a pressure of air that varies depending on respiration of a patient can be measured.

The flow rate sensor 23 is a sensor for measuring a flow rate of air between the CPAP apparatus 10 and another end of the air passage member (hose 20). In addition, the flow rate sensor 23 can measure a flow rate of air that varies depending on respiration of a patient in order to measure a flow rate in the closed air flow path (including the patient wearing the mask 30 located at the other end of the hose 20) including the CPAP apparatus 10 and the air passage member (hose 20) that communicates with the exhaust outlet (connection portion 13). In the CPAP apparatus 10 according to the present embodiment, by using a value measured by at least one of the pressure sensor 22 and the flow rate sensor 23, a command value for controlling a rotation number of the fan 16 is corrected such that a pressure of air expelled by the air supply unit 15 becomes a target pressure.

A rotation number of the fan 16 can be obtained by detecting a rotor position of the motor 17 for driving the fan 16 by a hall sensor 24. Specifically, the CPU 191 measures a rotation number of the fan 16 based on a detection signal from the hall sensor 24 obtained through the motor driving unit 193.

(Control of Apparatus)

Figure 4A:
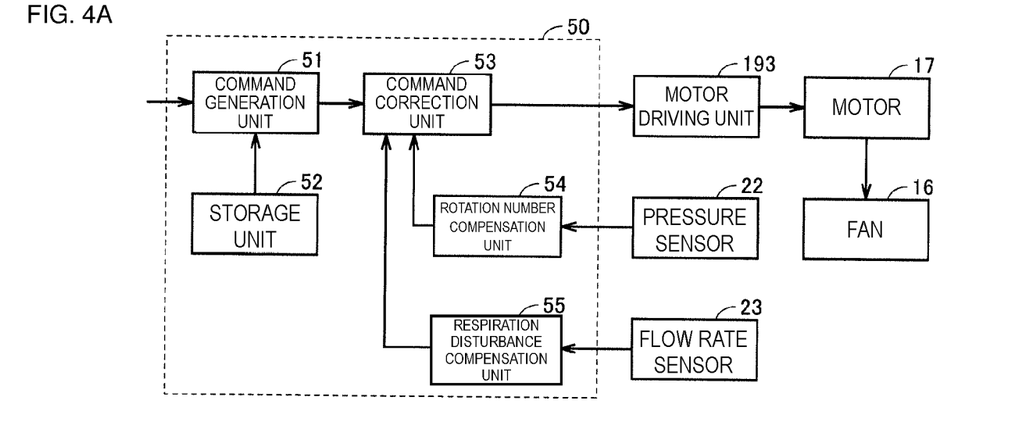
FIGS. 4A and 4B are block diagrams for explaining a function of a control unit of the CPAP apparatus according to the embodiment of the present disclosure.
Figure 4B:
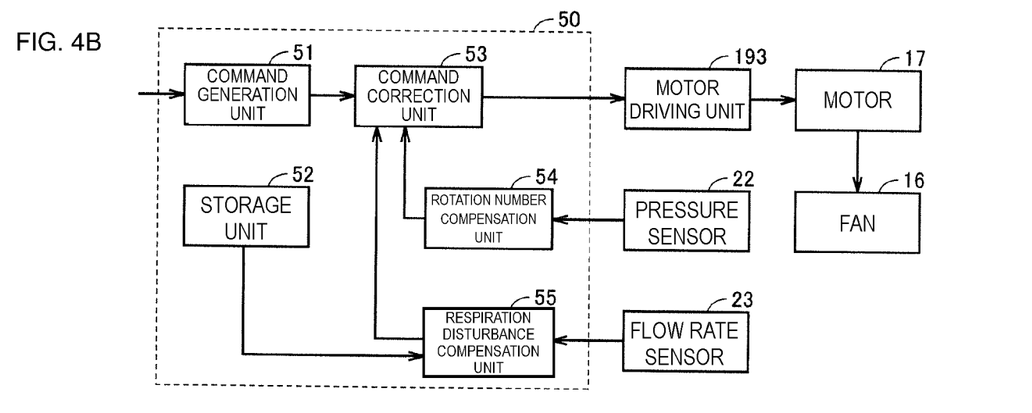

Next, control of a rotation number of the fan 16 performed by the CPAP apparatus 10 such that a pressure of air expelled by the air supply unit 15 becomes the target pressure will be described. The control of a rotation number of the fan 16 is performed by a circuit provided on the control board 19, and is performed by a control unit which will be described below. FIGS. 4A and 4B are block diagrams for explaining a control unit 50 (e.g. a processor or the like) of the CPAP apparatus 10 according to the embodiment of the present disclosure. The control unit 50 includes a command generation unit 51, a storage unit 52, a command correction unit 53, a rotation number compensation unit 54, and a respiration disturbance compensation unit 55.

The command generation unit 51 receives an operation of the operation buttons 12, and generates a command value of a rotation number of the fan 16 such that a pressure of air expelled by the air supply unit 15 becomes the target pressure. A pressure of air expelled by the air supply unit 15 has correlation characteristic with a flow rate of air between the CPAP apparatus 10 and the other end of the air passage member (hose 20), and follows a P-Q curve (static pressure-flow rate curve) to be determined due to an internal shape of the housing 14, performance inherent in the air supply unit 15, and a rotation number (rotation speed) of the fan 16.

Figure 5:
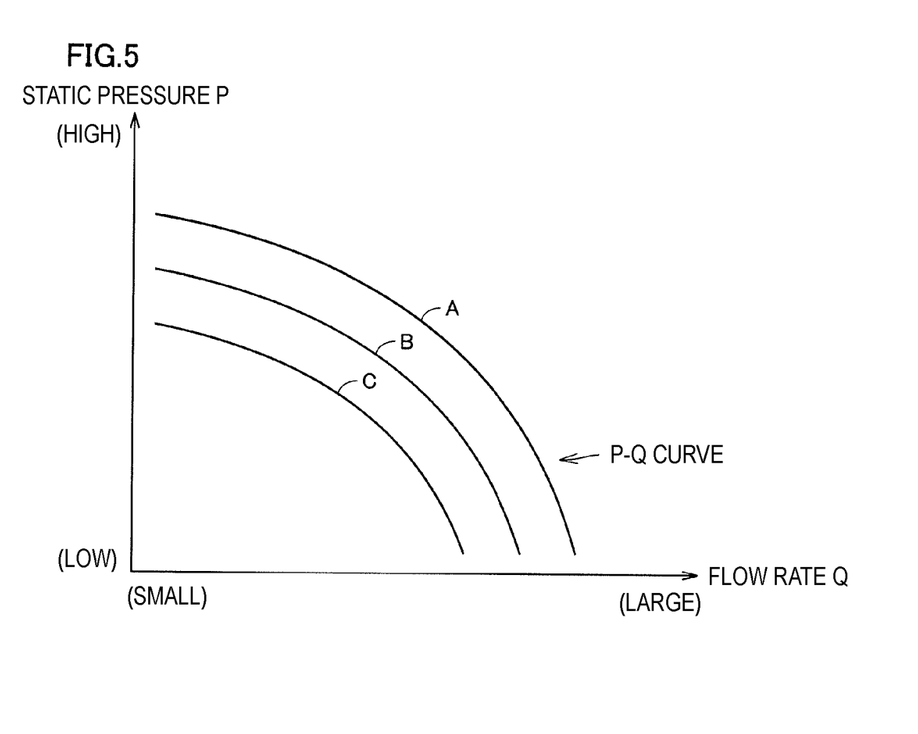
FIG. 5 is a graph showing examples of P-Q curves of an air supply unit.

Here, the P-Q curve is correlation characteristic indicating a relationship between a pressure and a flow rate of air generated by the fan 16. FIG. 5 is a graph showing examples of P-Q curves of the air supply unit 15. In FIG. 5, a flow rate Q is set in a horizontal axis and a static pressure P is set in a vertical axis. Note that the static pressure P is a pressure loss in the air flow path from the CPAP apparatus 10 through the mask 30 to the airway and lungs of a patient, and varies depending on respiration of the patient. For example, when a patient inhales (inhalation), the lungs expand and increase in volume to decrease the static pressure P, and when the patient exhales (exhalation), the lungs contract and decrease in volume to increase the static pressure P.

A P-Q curve of the air supply unit 15 differs depending on a rotation number of the fan 16 as long as the same air supply unit 15 is used. For example, in the P-Q curves shown in FIG. 5 three curves are shown when the rotation numbers of the fan 16 are different. Specifically, the rotation numbers of the fan 16 are reduced in order of a curve A, a curve B, and a curve C. That is, as a rotation number of the fan 16 increases, the flow rate Q of the air supply unit 15 also increases, as long as the static pressure P is the same.

Information of P-Q curves is stored in the storage unit 52. A configuration is illustrated in which the storage unit 52 shown in FIG. 4A inputs the information of the P-Q curves to the command generation unit 51, and the information of the P-Q curves is provided from the command generation unit 51 to the command correction unit 53. On the other hand, a configuration is illustrated in which the storage unit 52 shown in FIG. 4B directly inputs the information of the P-Q curves to the respiration disturbance compensation unit 55. Of course, the storage unit 52 may input the information of the P-Q curves to the command generation unit 51 and the respiration disturbance compensation unit 55. Also, the storage unit 52 is configured so as to correspond to the ROM/RAM 192 shown in FIG. 3, but may also be an external storage device (for example, an SSD, an HDD, or the like) connected to the CPU 191, separately from the ROM/RAM 192. Description will be given below based on assumption that the information of the P-Q curve is stored in the storage unit 52 for each different rotation number of the fan 16, however, the information of the P-Q curves may be stored only for the main rotation numbers of the fan 16 or information of a generalized P-Q curve which does not depend on a rotation number of the fan 16 may be stored.

When the information of the P-Q curves is stored in the storage unit 52 only for the main rotation numbers of the fan 16, the CPU 191 performs a known interpolation operation on the stored information to calculate the information of the P-Q curve corresponding to the required rotation number of the fan 16. When the information of the generalized P-Q curve that does not depend on a rotation number of the fan 16 is stored in the storage unit 52, the CPU 191 calculates the required rotation number of the fan 16 based on the information of the generalized P-Q curve.

The command correction unit 53 corrects a command value generated by the command generation unit 51 based on values measured by the pressure sensor 22 and the flow rate sensor 23. The pressure sensor 22 measures a pressure of air expelled by the air supply unit 15, and outputs the measured value to the rotation number compensation unit 54. The rotation number compensation unit 54 calculates a pressure difference between the pressure value obtained by the pressure sensor 22 and the target pressure, and calculates a correction value for correcting the command value in response to the pressure difference.

In other words, the rotation number compensation unit 54 performs feedback control such that the pressure difference between the pressure value obtained by the pressure sensor 22 and the target pressure becomes 0 (zero). However, in the rotation number compensation unit 54, pressure fluctuation accompanying respiration of a patient is corrected by follow-up, so that the return to the target pressure is delayed.

On the other hand, the flow rate sensor 23 measures a flow rate of air expelled by the air supply unit 15, and outputs the measured value to the respiration disturbance compensation unit 55. The respiration disturbance compensation unit 55 obtains the flow rate value from the flow rate sensor 23, and calculates a correction value for correcting the command value such that a pressure of air to be delivered to the patient becomes the target pressure. Specifically, when the patient inhales (inhalation) or when the patient exhales (exhalation), the respiration disturbance compensation unit 55 derives a required correction value (rotation number) by referring to the P-Q curve generalized from the flow rate value obtained by the flow rate sensor 23 and the target pressure.

That is, in the respiration disturbance compensation unit 55, feed-forward control is performed such that the flow rate value obtained by the flow rate sensor 23 becomes the target pressure. Therefore, the respiration disturbance compensation unit 55 can quickly correct the pressure fluctuation caused by the respiration of the patient, and can perform control for maintaining the target pressure without necessarily causing a delay in correction as in the case of the rotation number compensation unit 54.

The correction value calculated by the rotation number compensation unit 54 and the correction value calculated by the respiration disturbance compensation unit 55 are output to the command correction unit 53. The command correction unit 53 determines a command value to be output to the motor driving unit 193 in consideration of the correction values calculated by the rotation number compensation unit 54 and the respiration disturbance compensation unit 55, with respect to the command value generated by the command generation unit 51.

Note that the command correction unit 53 may change a percentage of the correction values to be considered with respect to the command value generated by the command generation unit 51. For example, the command value output to the motor driving unit 193 is determined by combining 80% of a command value generated by the command generation unit 51 and a correction value calculated by the respiration disturbance compensation unit 55 with 20% of a correction value of the rotation number compensation unit 54. Moreover, when a correction value of the respiration disturbance compensation unit 55 is strongly taken into consideration with respect to a command value generated by the command generation unit 51, the command correction unit 53 determines a command value to be output to the motor driving unit 193 by combining 70% of the generated command value, 10% of the correction value of the rotation number compensation unit 54, and 20% of the correction value of the respiration disturbance compensation unit 55.

The motor driving unit 193 supplies a DC voltage to the motor 17 so as to reach the rotation number of the fan 16 based on the command value output from the command correction unit 53. The motor 17 rotates the fan 16 according to the DC voltage supplied from the motor driving unit 193. Air expelled from the fan 16 passes through the hose 20 to the mask 30 and reaches the airway and lungs of the patient.

(Control Flowchart)

Figure 6:
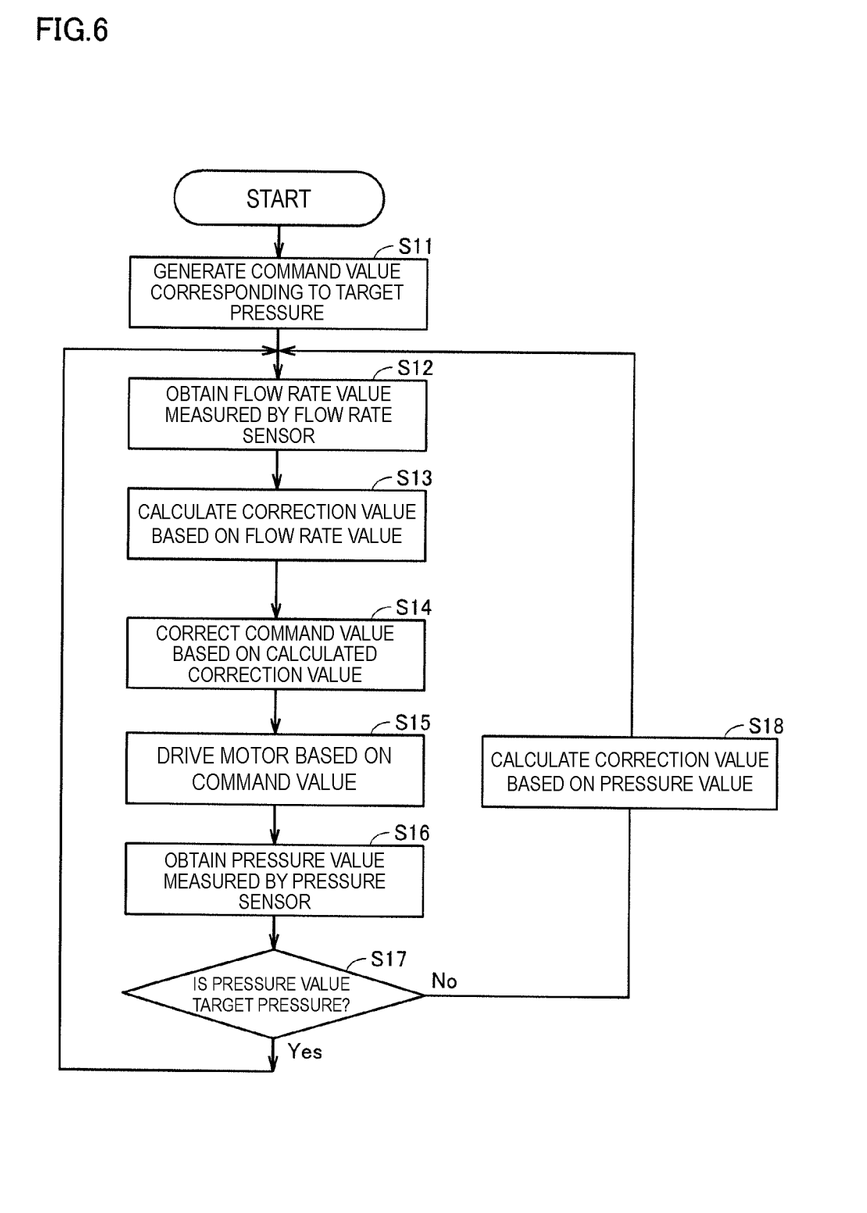
FIG. 6 is a flowchart for explaining control of the CPAP apparatus according to the embodiment of the present disclosure.

The control of the air supply unit 15 in the control unit 50 shown in FIGS. 4A and 4B will be described with reference to a flowchart. FIG. 6 is a flowchart for explaining the control of the CPAP apparatus 10 according to the embodiment of the present disclosure. The control unit 50 of the CPAP apparatus 10 starts control such that a pressure of air to be expelled from the other end of the hose 20 becomes the target pressure when a patient presses the operation button 12.

First, the control unit 50 generates a command value corresponding to the target pressure (step S11). Specifically, the command generation unit 51 shown in FIGS. 4A and 4B generate the command value corresponding to the target pressure based on a pressure setting value input in advance.

Next, the control unit 50 obtains a flow rate value measured by the flow rate sensor 23 (step S12). The control unit 50 calculates a correction value based on the obtained flow rate value (step S13). Specifically, the respiration disturbance compensation unit 55 shown in FIGS. 4A and 4B calculates a correction value for correcting the command value such that a pressure of air to be delivered to the patient becomes the target pressure based on a flow rate value obtained by the flow rate sensor 23 and the P-Q curve.

Next, the control unit 50 generates a command value to be output based on the command value generated in step S11 and the correction value calculated in step S13 (step S14). In other words, the control unit 50 generates the command value in consideration of the correction value calculated in step S13. The control unit 50 outputs the command value generated in step S14 to the motor driving unit 193, thereby driving the motor 17 so as to become a rotation number of the fan 16 instructed by the command value (step S15).

Next, the control unit 50 obtains a pressure value measured by the pressure sensor 22 (step S16). The control unit 50 determines whether or not the obtained pressure value is the target pressure (step S17). When the pressure value is not the target pressure (step S17: NO), the control unit 50 calculates a correction value based on the obtained pressure value as feedback control (step S18). Specifically, the rotation number compensation unit 54 shown in FIGS. 4A and 4B calculates a pressure difference between the pressure value obtained by the pressure sensor 22 and the target pressure, and calculates a correction value for correcting the command value according to the pressure difference. After the processing in step S18, the processing returns to step S12, and the control unit 50 generates a command value to be output in consideration of the correction value calculated in step S13 and the correction value calculated in step S18.

On the other hand, when the pressure value is the target pressure (step S17: YES), the control unit 50 returns the processing to step S12. Thereafter, the control unit 50 repeats the processing of step S11 to step S18 until an operation end by the patient pressing the operation button 12 is received, or a period of time of the set timer elapses.

(Control Result)

Figure 7:
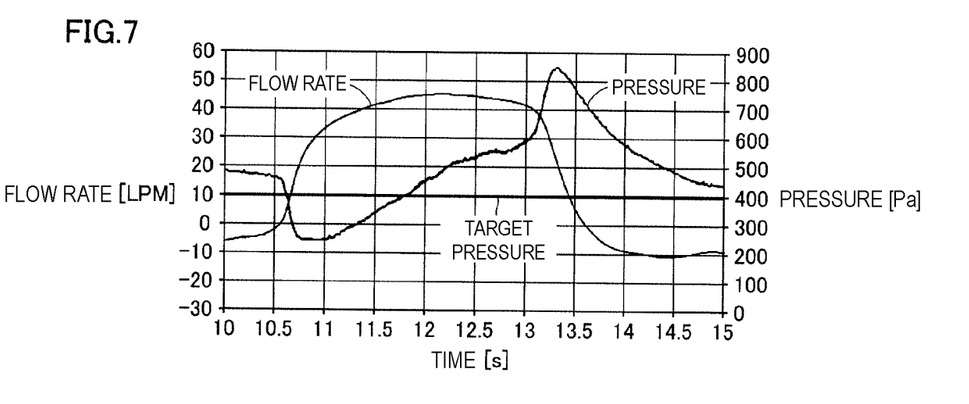
FIG. 7 is a diagram showing a control result by the CPAP apparatus based on only a pressure value obtained by a pressure sensor.
Figure 8:
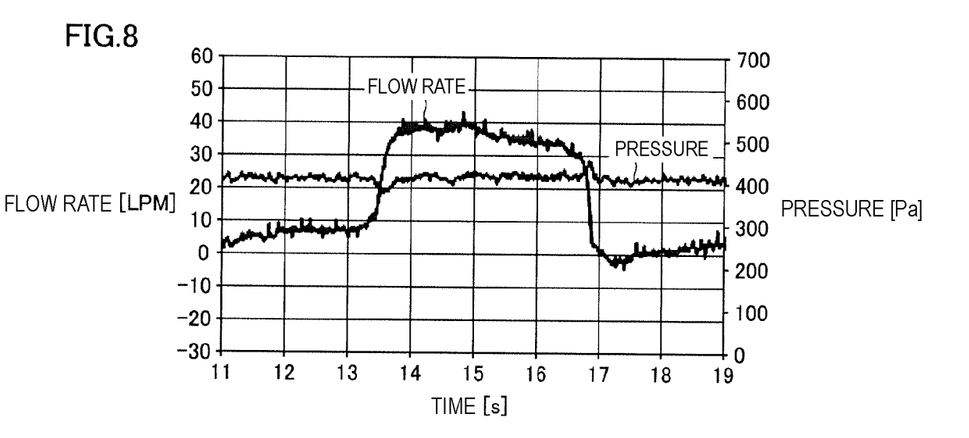
FIG. 8 is a diagram showing a control result by the CPAP apparatus according to the embodiment of the present disclosure.

Next, description will be given by comparing between control results of a case where the air supply unit 15 is controlled based on only a pressure value obtained by the pressure sensor 22 and a case where the air supply unit 15 is controlled based on a pressure value obtained by the pressure sensor 22 and a flow rate value obtained by the flow rate sensor 23 as described in the present embodiment. FIG. 7 is a diagram showing a control result by the CPAP apparatus based on only a pressure value obtained by the pressure sensor 22. FIG. 8 is a diagram showing a control result by the CPAP apparatus 10 according to the embodiment of the present disclosure. In addition, it is assumed that in the control result shown in FIG. 7, the target pressure is set to 400 Pa, and in the control result shown in FIG. 8, the target pressure is also set to 400 Pa. Note that in FIG. 7 and FIG. 8, a unit of time is expressed by [s] as second, a unit of flow rate is expressed by [LPM] as liter/min, and a unit of pressure is expressed by [Pa] as pascal.

In the control result shown in FIG. 7, the flow rate suddenly increases when the patient starts to inhale at around the time of 10.5 seconds, and the pressure rapidly decreases. Therefore, the control unit 50 of the CPAP apparatus 10 performs feedback control based on a pressure value obtained by the pressure sensor 22, thereby increasing a rotation number of the fan in order to return the pressure to the target pressure. However, when the control unit 50 performs control of the air supply unit 15 only by the feedback control, since the rotation number of the fan is increased by follow-up based on the pressure value measured by the pressure sensor 22, a delay in the control for returning the pressure to the target pressure occurs. Specifically, in the control result shown in FIG. 7, the pressure is changed to increase at around the time of 11 seconds. When such control is performed, the pressure does not reach the target pressure even though the patient inhales, so that the CPAP apparatus 10 may not sufficiently open the airway of the patient.

In addition, in the control result shown in FIG. 7, due to the fact that the patient starts to exhale at around the time of 13.2 seconds, even though the flow rate is suddenly reduced, the pressure continues to rise up to about the time of 13.4 seconds because of the delay in the control of the control unit 50. When such control is performed, even though the patient exhales, the pressure is higher than the target pressure, so that it becomes difficult for the patient to exhale.

On the other hand, in the CPAP apparatus 10 according to the present embodiment, not only feedback control is performed based on a pressure value obtained by the pressure sensor 22 but also feed-forward control is performed based on a flow rate value obtained by the flow rate sensor 23. In the control result shown in FIG. 8, the flow rate is suddenly increased by the fact that the patient starts to inhale around the time of 13.5 seconds, but the feed-forward control is performed based on the flow rate value obtained by the flow rate sensor 23, thereby rapidly increasing the rotation number of the fan 16. Therefore, the control unit 50 maintains the pressure substantially at the target pressure regardless of the inhalation of the patient. When such control is performed, even when the patient inhales, the pressure is maintained at the target pressure, so that the CPAP apparatus 10 can open the airway of the patient and deliver air to the airway and the lungs.

In addition, in the control result shown in FIG. 8, the flow rate is rapidly decreased by the fact that the patient starts to exhale at around the time of 16.8 seconds, but the rotation number of the fan 16 is quickly reduced by the feed-forward control of the control unit 50. Therefore, the control unit 50 maintains the pressure substantially at the target pressure regardless of the exhalation of the patient. When such control is performed, even when the patient exhales, the pressure is maintained at the target pressure, so that it is easy for the patient to exhale.

As described above, the CPAP apparatus 10 according to the present embodiment includes the housing 14 having the intake port 18 and the connection portion 13, the hose 20 whose one end communicates with the connection portion 13, the fan 16 which expels air flowing in from the intake port 18, from the other end of the hose 20, the motor 17 and the motor driving unit 193 which rotationally drive the fan 16, the control unit 50 which controls the motor driving unit 193, and the flow rate sensor 23. The control unit 50 includes the command generation unit 51 for generating a command value of a rotation number of the fan 16 such that a pressure for expelling air from the other end of the hose 20 becomes the target pressure, and the command correction unit 53 for correcting the command value based on a flow rate value obtained by the flow rate sensor 23. Also, the command generation unit 51 generates a command value by a pressure of air generated by rotational driving of the fan 16. Additionally, the command value is a signal that is output from the control unit 50 to be input to the motor driving unit 193, and that is for setting a rotation number of the fan 16 to a designated value.

Therefore, in the CPAP apparatus 10, due to the correction based on a flow rate value obtained by the flow rate sensor 23, a pressure of air to be expelled can be controlled to become the target pressure regardless of a flow rate of the inhalation or exhalation of the patient.

The command correction unit 53 and the respiration disturbance compensation unit 55 calculate a change in a pressure of air to be delivered to the other end of the hose 20 from a change in a flow rate value obtained by the flow rate sensor 23, and correct the command value such that the pressure of the air delivered to the other end of the hose 20 becomes the target pressure. Specifically, the respiration disturbance compensation unit 55 obtains a flow rate value from the flow rate sensor 23, and calculates a correction value for correcting the command value such that the pressure of the air to be delivered to the patient becomes the target pressure. The command correction unit 53 corrects the command value in consideration of the correction value calculated by the respiration disturbance compensation unit 55.

Specifically, the command correction unit 53 derives a required correction value (rotation number) by referring to the P-Q curve generalized a flow rate value obtained by the flow rate sensor 23 and the corresponding target pressure. For example, during inhalation, the command correction unit 53 corrects the command value such that a rotation number of the fan 16 increases, because the rotation number of the fan 16 at the time of measuring the flow rate value is smaller than the designated rotation number of the fan 16 shown in the P-Q curve corresponding to the flow rate value obtained by the flow rate sensor 23 and the target pressure. Further, for example, during exhalation, the command correction unit 53 corrects the command value such that a rotation number of the fan 16 decreases, because the rotation number of the fan 16 at the time of measuring the flow rate value is larger than the designated rotation number of the fan 16 shown in the P-Q curve corresponding to the flow rate value obtained by the flow rate sensor 23 and the target pressure.

The CPAP apparatus 10 according to the present embodiment further includes the pressure sensor 22 as shown in FIG. 3. Therefore, the command correction unit 53 and the rotation number compensation unit 54 correct the command value generated by the command generation unit 51 based on a pressure value obtained by the pressure sensor 22. Therefore, the CPAP apparatus 10 can be controlled more accurately such that a pressure of air to be expelled becomes the target pressure in comparison with a CPAP apparatus provided with only a flow rate sensor.

The command correction unit 53 and the rotation number compensation unit 54 calculate a pressure difference between a pressure value obtained by the pressure sensor 22 and the target pressure, and correct the command value according to the pressure difference. Specifically, when a pressure value obtained by the pressure sensor 22 is smaller than the target pressure, the command correction unit 53 corrects the command value so as to increase a rotation number of the fan 16. In addition, when a pressure value obtained by the pressure sensor 22 is larger than the target pressure, the command correction unit 53 corrects the command value so as to decrease a rotation number of the fan 16.

(Modifications)

(1) The CPAP apparatus 10 according to the present embodiment includes not only a configuration for performing feed-forward control based on a flow rate value obtained by the flow rate sensor 23 but also a configuration for performing feedback control based on a pressure value obtained by the pressure sensor 22. However, the present disclosure is not limited thereto, and the CPAP apparatus may include only a configuration for performing feed-forward control based on a flow rate value obtained by the flow rate sensor 23. Moreover, in addition to the configuration for performing the feed-forward control based on a flow rate value obtained by the flow rate sensor 23, the CPAP apparatus may include a configuration for performing another feed-forward control and a configuration for performing feedback control.

(2) In the CPAP apparatus 10 according to the present embodiment, information of P-Q curves (information of correlation characteristics) representing a relationship between a pressure of air generated by the fan 16 and a flow rate is stored in the storage unit 52. However, the storage unit 52 may store information of P-Q curves related to only main rotation numbers of the fan 16, and may store information of the generalized P-Q curve which does not depend on a rotation number of the fan 16. This makes it possible to reduce a storage capacity of the storage unit 52.

(3) In the CPAP apparatus 10 according to the present embodiment, it has been described that the target pressure is a constant value regardless of exhalation and inhalation of a patient. However, the present disclosure is not limited thereto, and in the CPAP apparatus, the target pressure may be set so as to vary depending on the exhalation or the inhalation of the patient.

(4) In the CPAP apparatus 10 according to the present embodiment, the pressure sensor 22 and the flow rate sensor 23 are provided in a vicinity of the air flow outlet of the air supply unit 15. However, the present disclosure is not limited thereto, and a pressure sensor or a flow rate sensor may be provided in or on the hose 20 or the mask 30 which is provided closer to the patient. The CPAP apparatus is not limited to a configuration in which one pressure sensor and one flow rate sensor are provided, and a plurality of pressure sensors and a plurality of flow rate sensors may be provided.

Figure 9:
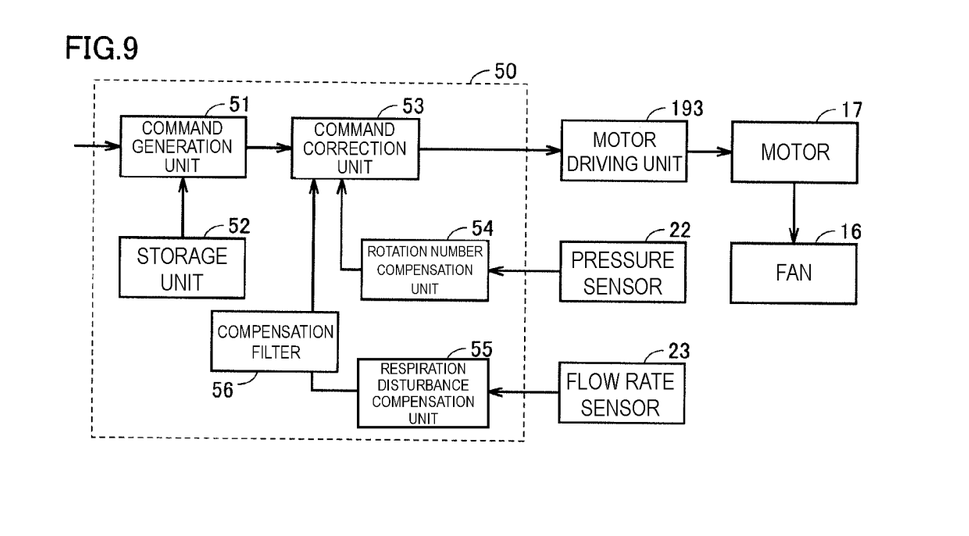
FIG. 9 is a block diagram for explaining a control unit of a CPAP apparatus according to a modification.

(5) In the CPAP apparatus 10 according to the present embodiment, a configuration in which a signal from the respiration disturbance compensation unit 55 is directly input to the command correction unit 53 as shown in FIGS. 4A and 4B has been described. However, when a signal from the respiration disturbance compensation unit 55 is directly input to the command correction unit 53, there is a possibility of oscillation, so that the signal from the respiration disturbance compensation unit 55 may be input to the command correction unit 53 via a filter. FIG. 9 is a block diagram for explaining a control unit 50A of a CPAP apparatus according to a modification. The control unit 50A includes the command generation unit 51, the storage unit 52, the command correction unit 53, the rotation number compensation unit 54, the respiration disturbance compensation unit 55, and a compensation filter 56. Note that in a configuration shown in FIG. 9, the same constituent elements as those shown in FIGS. 4A and 4B are denoted by the same reference signs, and detailed description thereof will be omitted.

The compensation filter 56 is a filter circuit for blunting a waveform of a signal from the respiration disturbance compensation unit 55, and is, for example, a low pass filter circuit. The compensation filter 56 may employ a band pass filter circuit, a high pass filter circuit, or the like according to a signal whose waveform is blunted. The command correction unit 53 suppresses occurrence of oscillation by inputting a waveform of a signal blunted by the compensation filter 56 from the respiration disturbance compensation unit 55.

(6) In the CPAP apparatus 10 according to the present embodiment, as shown in FIGS. 4A and 4B, the command generation unit 51 and the respiration disturbance compensation unit 55 are individually provided, and a command value is corrected in the command correction unit 53 based on operation results that are separately performed, and then the corrected command value is output to the motor driving unit 193. However, the CPAP apparatus may have a configuration in which an amount of operations is reduced by integrating the command generation unit 51 and the respiration disturbance compensation unit 55. Hereinafter, a configuration in which the command generation unit 51 and the respiration disturbance compensation unit 55 are integrated will be described.

Figure 10:
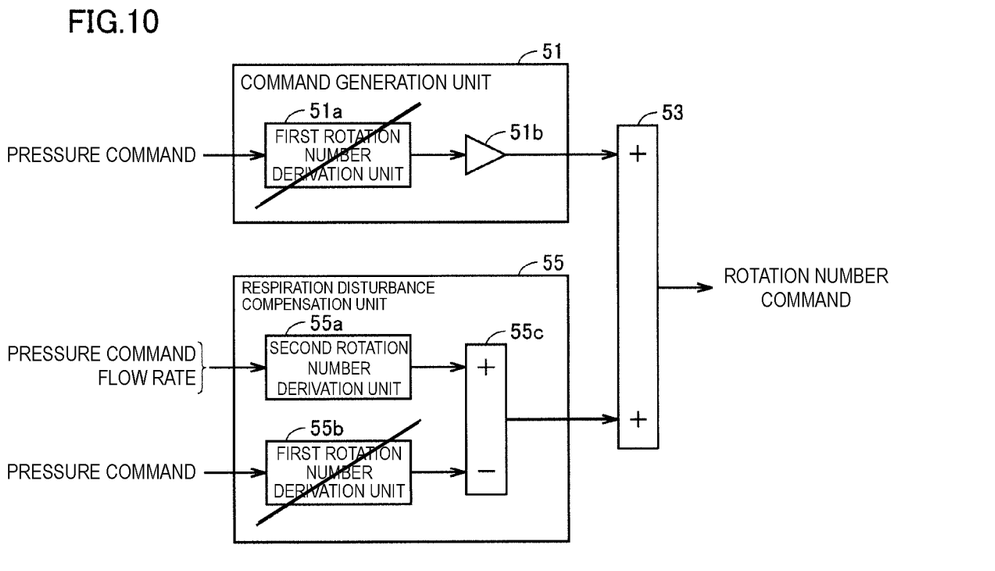
FIG. 10 is a block diagram for explaining operations in a command generation unit and a respiration disturbance compensation unit.

FIG. 10 is a block diagram for explaining operations in the command generation unit 51 and the respiration disturbance compensation unit 55. The command generation unit 51 includes a first rotation number derivation unit 51a for calculating a rotation number of the fan 16 required for a pressure to become the target pressure at a flow rate of zero, based on a pressure command for commanding the target pressure. Further, the command generation unit 51 includes an FF coefficient unit 51b which multiplies a value calculated by the first rotation number derivation unit 51a by an FF (feed-forward) coefficient of feed-forward control. The command generation unit 51 outputs the value multiplied by the FF coefficient in the FF coefficient unit 51b as a rotation number command.

The respiration disturbance compensation unit 55 includes a second rotation number derivation unit 55a for calculating a rotation number of the fan 16 required for a pressure to become the target pressure at the measured flow rate, based on a pressure command for commanding the target pressure and the flow rate measured by the flow rate sensor 23. Further, the respiration disturbance compensation unit 55 includes a first rotation number derivation unit 55b for calculating a rotation number of the fan 16 required for a pressure to become the target pressure at a flow rate of zero, based on a pressure command for commanding the target pressure. In the respiration disturbance compensation unit 55, a difference between values output from the second rotation number derivation unit 55a and the first rotation number derivation unit 55b is derived in a difference derivation unit 55c, and is output as a rotation number command.

The command correction unit 53 outputs a rotation number command to the motor driving unit 193 by using the rotation number command output from the respiration disturbance compensation unit 55 and the rotation number command output from the command generation unit 51.

As can be seen from FIG. 10, the first rotation number derivation unit 51a in the command generation unit 51 and the first rotation number derivation unit 55b in the respiration disturbance compensation unit 55 perform the same operation, and the operation processes are duplicated. Therefore, by integrating the command generation unit 51 and the respiration disturbance compensation unit 55, it is possible to reduce the duplicated operation processes.

Figure 11:
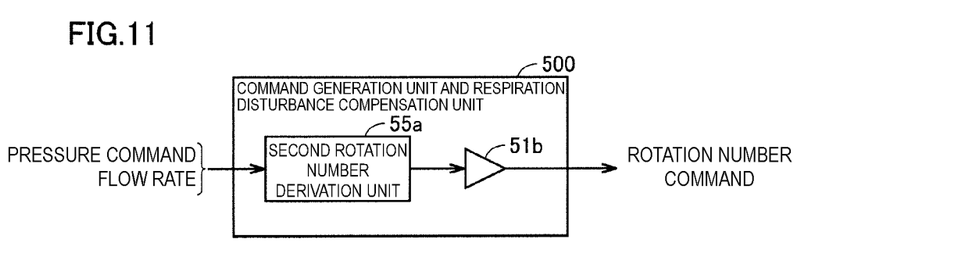
FIG. 11 is a block diagram for explaining an operation in a processing unit in which the command generation unit and the respiration disturbance compensation unit are integrated.

FIG. 11 is a block diagram for explaining an operation of a processing unit 500 in which the command generation unit 51 and the respiration disturbance compensation unit 55 are integrated. The processing unit 500 has only a configuration in which an operation in the first rotation number derivation unit 51a and an operation in the first rotation number derivation unit 55b cancel each other, and the second rotation number derivation unit 55a and the FF coefficient unit 51b are included. Therefore, the processing unit 500 can reduce the operation processing in comparison with a case where the command generation unit 51 and the respiration disturbance compensation unit 55 are not integrated.

(7) Further, a CPAP apparatus may be configured in which the command generation unit 51, the rotation number compensation unit 54, and the respiration disturbance compensation unit 55 are integrated to reduce an amount of operations. Hereinafter, a configuration in which the command generation unit 51, the rotation number compensation unit 54, and the respiration disturbance compensation unit 55 are integrated will be described with reference to the drawings.

Figure 12:
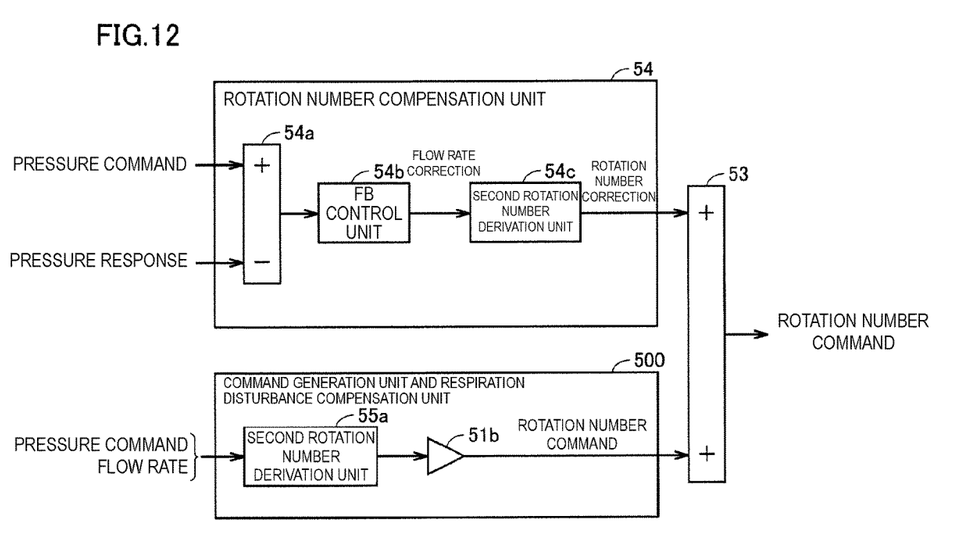
FIG. 12 is a block diagram for explaining the operations in the processing unit in which the command generation unit and the respiration disturbance compensation unit are integrated and a rotation number compensation unit.

FIG. 12 is a block diagram for explaining operations of the processing unit 500 in which the command generation unit 51 and the respiration disturbance compensation unit 55 are integrated, and the rotation number compensation unit 54. The processing unit 500 includes the second rotation number derivation unit 55a and the FF coefficient unit 51b. That is, the processing unit 500 performs feed-forward control.

The rotation number compensation unit 54 includes a pressure difference derivation unit 54a for deriving a difference between a pressure command for commanding the target pressure and a pressure response measured by the pressure sensor 22, and a feedback control unit 54b for calculating a correction value of a flow rate from a pressure difference value derived by the pressure difference derivation unit 54a. Further, the rotation number compensation unit 54 includes a second rotation number derivation unit 54c for calculating the rotation number of the fan 16 required for a pressure to become the target pressure at a current flow rate based on a pressure command for commanding the target pressure and the correction value of the flow rate calculated in the feedback control unit 54b. That is, the rotation number compensation unit 54 performs feedback control.

The command correction unit 53 outputs a rotation number command to motor driving unit 193 by using the rotation number command output from the rotation number compensation unit 54 and the rotation number command output from the processing unit 500.

As can be seen from FIG. 12, the second rotation number derivation unit 54c in the rotation number compensation unit 54 and the second rotation number derivation unit 55a in the processing unit 500 perform the same operation, and the operation processes are duplicated. Therefore, the command generation unit 51, the rotation number compensation unit 54, and the respiration disturbance compensation unit 55 are integrated, thereby reducing the duplicated operation processes.

Figure 13:
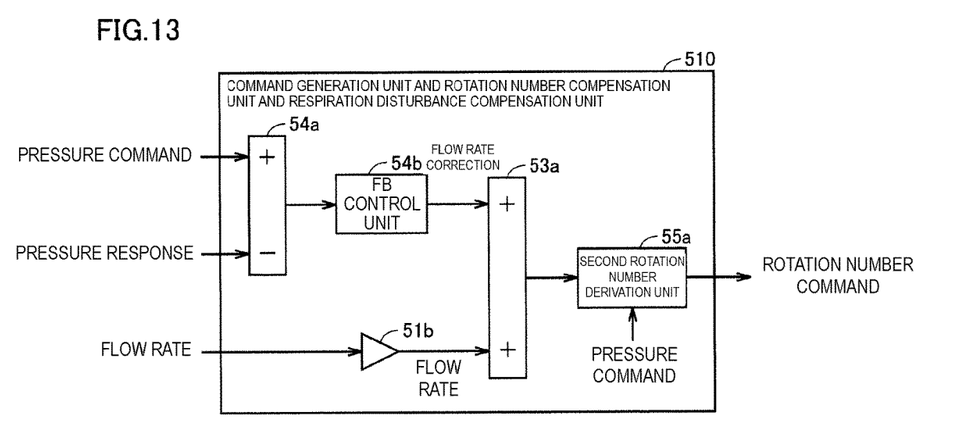
FIG. 13 is a block diagram for explaining an operation in a processing unit in which the command generation unit, the rotation number compensation unit, and the respiration disturbance compensation unit are integrated.

FIG. 13 is a block diagram for explaining an operation of a processing unit 510 in which the command generation unit 51, the rotation number compensation unit 54, and the respiration disturbance compensation unit 55 are integrated. In the processing unit 510, in a process of calculating a rotation number command from a flow rate, by integrating a process of feedback control of the rotation number compensation unit 54 and a process of feed-forward control of the processing unit 500, so that the second rotation number derivation unit 54c and the second rotation number derivation unit 55a whose operation processes are duplicated are integrated. Operation processing of the processing unit 510 can be reduced by integrating the second rotation number derivation unit 54c and the second rotation number derivation unit 55a whose operation processes are duplicated.

Note that, as for the second rotation number derivation unit 55a, a correction value of a flow rate derived from a pressure difference in the feedback control unit 54b and a value obtained by multiplying a flow rate measured by the flow rate sensor 23 by the FF coefficient in the FF coefficient unit 51b are regarded as a flow rate to be input. That is, a flow rate to be input to the second rotation number derivation unit 55a is a flow rate for which the feed-forward control process and the feedback control process have already been executed.

It should be understood that the embodiment disclosed herein is illustrative and is not limited in all respects. The scope of the present disclosure is indicated by the appended claims rather than by the above description and is intended to include all modifications within the meaning and scope equivalent to those of the appended claims.

REFERENCE SIGNS LIST

10 CPAP APPARATUS
11 DISPLAY UNIT
12 OPERATION BUTTON
13 CONNECTION PORTION
14 HOUSING
15 AIR SUPPLY UNIT
16 FAN
17 MOTOR
18 INTAKE PORT
19 CONTROL BOARD
20 HOSE
21 AC ADAPTER
22 PRESSURE SENSOR
23 FLOW RATE SENSOR
24 HALL SENSOR
30 MASK
50 CONTROL UNIT
51 COMMAND GENERATION UNIT
52 STORAGE UNIT
53 COMMAND CORRECTION UNIT
54 ROTATION NUMBER COMPENSATION UNIT
55 RESPIRATION DISTURBANCE COMPENSATION UNIT
192 ROM/RAM
193 MOTOR DRIVING UNIT

The invention claimed is:

1. A CPAP apparatus comprising:
a housing comprising an intake inlet and an exhaust outlet;
an air passage comprising a first end connected to the exhaust outlet;
a fan configured to expel air from a second end of the air passage, the air flowing into the CPAP apparatus at the intake inlet;
a fan driver configured to rotationally drive the fan according to a rotational parameter;
a processor configured to control the fan driver;
a flow rate sensor configured to measure an air flow rate between the fan and the second end of the air passage; and
a pressure sensor configured to measure a pressure of air between the fan and the second end of the air passage,
wherein the processor is configured to:
generate a command value corresponding to the rotational parameter of the fan at which a pressure of air expelled from the exhaust outlet is equal to a target pressure,
determine a change in a pressure of air delivered to the air passage based on a change in the measured air flow rate, and a respiration disturbance correction value based on the determined change in pressure,
determine a pressure difference between the measured pressure and the target pressure, and a rotation number correction value based on the determined pressure difference,
correct the command value based on a weighted combination of the command value, the respiration disturbance correction value, and the rotation number correction value, such that the pressure of air delivered to the air passage equals the target pressure.

2. The CPAP apparatus according to claim 1, wherein the processor is configured to generate the command value based on a pressure of air generated by rotationally driving the fan.

3. The CPAP apparatus according to claim 1, wherein:
the command value is output as a signal from the processor and is input to the fan driver, and
the fan driver is configured to drive the fan at the rotational parameter based on the command value.

4. The CPAP apparatus according to claim 1, further comprising:
memory configured to store information indicative of a relationship between a pressure of air and a flow rate of air generated by the fan.

5. The CPAP apparatus according to claim 4, wherein:
the stored information further relates the pressure of air and the flow rate of air generated by the fan to a corresponding rotational parameter,
when the rotational parameter of the fan when the measured air flow rate is less than the rotational parameter of the fan stored in memory and related to the measured air flow rate at the target pressure, the processor is configured to correct the command value such that the rotational parameter of the fan increases, and
when the rotational parameter of the fan when the measured air flow rate is greater than the rotational parameter of the fan stored in memory and related to the measured air flow rate at the target pressure, the processor is configured to correct the command value such that the rotational parameter of the fan decreases.

6. The CPAP apparatus according to claim 1, wherein:
when the measured pressure is less than the target pressure, the processor is configured to correct the command value such that the rotational parameter of the fan increases, and
when the measured pressure is greater than the target pressure, the processor is configured to correct the command value such that the rotational parameter of the fan decreases.

7. The CPAP apparatus according to claim 1, wherein the target pressure is a constant value for exhalation and inhalation of a patient.

8. The CPAP apparatus according to claim 1, wherein the command value and the respiration disturbance correction value are collectively weighted at 80%, and the rotation number correction value is weighted at 20%.

9. The CPAP apparatus according to claim 1, wherein the command value is weighted at 70%, the rotation number correction value is weighted at 10%, and the respiration disturbance correction value is weighted at 20%.

\* \* \* \* \*